(12) United States Patent
Ohtsuka

(10) Patent No.: US 7,701,579 B2
(45) Date of Patent: Apr. 20, 2010

(54) FLUORESCENCE SENSOR

(75) Inventor: Hisashi Ohtsuka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 34 days.

(21) Appl. No.: 12/038,976

(22) Filed: Feb. 28, 2008

(65) Prior Publication Data

US 2008/0204753 A1 Aug. 28, 2008

(30) Foreign Application Priority Data

Feb. 28, 2007 (JP) .............................. 2007-049324

(51) Int. Cl.
*G01N 21/25* (2006.01)
(52) U.S. Cl. ..................................... 356/417
(58) Field of Classification Search .............. 356/417, 356/73, 72, 317, 318; 250/458.1, 461.1
See application file for complete search history.

(56) References Cited

U.S. PATENT DOCUMENTS

2008/0192246 A1* 8/2008 Neiss et al. ................. 356/301

FOREIGN PATENT DOCUMENTS

JP 10-078390 A 3/1998

JP 3562912 B2 6/2004

OTHER PUBLICATIONS

Makio Tokunaga, 1. Total Internal Reflection Fluoresence Microscopy that Enables Observation of Surfaces Only with High Image Quality, Understanding with bio imaging, pp. 104-113.
Fang Yu et al., Surface Plasmon Field-Enhanced Fluorescence Spectroscopy Studies of the Interaction between an Antibody and Its Surface-Coupled Antigen, Analytical Chemistry, 2003, pp. 2610-2617, vol. 75.
Guang S. He et al., Optical limiting effect in a two-photon absorption dye doped solid matrix, Applied Physics Letters, 1995, pp. 2433-2435, vol. 67, Issue 23.

* cited by examiner

Primary Examiner—Tarifur Chowdhury
Assistant Examiner—Abdullahi Nur
(74) Attorney, Agent, or Firm—Sughrue Mion, PLLC

(57) ABSTRACT

A fluorescence sensor comprises a sensor section for collecting a fluorescent substance, which acts to represent presence of a substance to be detected in a sample, and an exciting light source, which produces exciting light for exciting the fluorescent substance to produce fluorescence. Besides the exciting light source, at least one different non-exciting light source is located for irradiating different non-exciting light, which varies in wavelength from the exciting light and which is substantially free from capability of exciting the fluorescent substance, to the sensor section.

9 Claims, 3 Drawing Sheets

FLUORESCENCE SENSOR

BACKGROUND OF THE INVENTION

1. Field of the Invention

This invention relates to a fluorescence sensor for detecting a specific substance, which is contained in a sample, by use of a fluorometric analysis technique.

2. Description of the Related Art

Heretofore, in fields of biological analyses, and the like, a fluorometric analysis technique has been used widely as an analysis technique, which has a high sensitivity and is easy to perform. The fluorometric analysis technique is the technique, wherein exciting light having a specific wavelength is irradiated to a sample expected to contain a substance to be detected, which substance is capable of producing fluorescence by being excited by the exciting light having the specific wavelength, wherein the fluorescence having thus been produced by the substance to be detected is detected, and wherein the presence of the substance to be detected is thereby confirmed. In cases where the substance to be detected is not a fluorescent substance, a technique has heretofore been conducted widely, wherein a specific binding substance, which has been labeled with a fluorescent substance and is capable of undergoing the specific binding with the substance to be detected, is brought into contact with the sample, wherein the fluorescence is detected in the same manner as that described above, and wherein the occurrence of the specific binding, i.e. the presence of the substance to be detected, is thereby confirmed.

FIG. 2 is a schematic side view showing an example of a conventional fluorescence sensor for carrying out a fluorometric analysis technique utilizing a labeled specific binding substance. By way of example, the fluorescence sensor illustrated in FIG. 2 is utilized for detecting an antigen 2, which is contained in a sample 1. The fluorescence sensor illustrated in FIG. 2 comprises a base plate 3, on which a primary antibody 4 capable of undergoing the specific binding with the antigen 2 has been coated. The fluorescence sensor also comprises a sample support section 5, which is formed on the base plate 3. The sample 1 is caused to flow within the sample support section 5. A secondary antibody 6, which has been labeled with a fluorescent substance 10 and is capable of undergoing the specific binding with the antigen 2, is then caused to flow within the sample support section 5. Thereafter, exciting light 8 is irradiated from an exciting light source 7 toward a surface area of the base plate 3. Also, an operation for detecting the fluorescence is performed by a photodetector 9. In cases where the predetermined fluorescence is detected by the photodetector 9, the specific binding of the secondary antibody 6 and the antigen 2 with each other, i.e. the presence of the antigen 2 in the sample, is capable of being confirmed.

In the example described above, the substance whose presence is actually confirmed with the fluorescence detecting operation is the secondary antibody 6. If the secondary antibody 6 does not undergo the specific binding with the antigen 2, the secondary antibody 6 will be carried away and will not be present on the base plate 3. Therefore, in cases where the presence of the secondary antibody 6 on the base plate 3 is detected, the presence of the antigen 2, which is the substance to be detected, is capable of being confirmed indirectly.

The confirmation of the presence of the secondary antibody 6 on the base plate 3 is also capable of being made with a technique wherein, instead of the photodetector 9 being used, the fluorescence is detected with visual observation made by persons. For example, in cases where a simple type fluorescence sensor, such as a fluorescence sensor for domestic use, is to be formed, the constitution in which the photodetector is not provided is capable of being employed appropriately, such that the cost may be kept low.

Particularly, with the rapid advances made in enhancement of performance of photodetectors, such as the advances made in cooled CCD image sensors, in recent years, the fluorometric analysis technique described above has become the means essential for biological studies. The fluorometric analysis technique has also been used widely in fields other than the biological studies. In particular, with respect to the visible region, as in the cases of FITC (fluorescence wavelength: 525 nm, quantum yield: 0.6), Cy5 (fluorescence wavelength: 680 nm, quantum yield: 0.3), and the like, fluorescent dyes having high quantum yields exceeding 0.2, which serves as a criterion for use in practice, have been developed. It is thus expected that the fields of the application of the fluorometric analysis technique will become wide even further.

However, with the conventional fluorescence sensor as illustrated in FIG. 2, the problems are encountered in that noise is caused to occur by the reflected/scattered exciting light at an interface between the base plate 3 and the sample 1 and the light scattered by impurities/suspended materials M, and the like, other than the substance to be detected. Therefore, with the conventional fluorescence sensor, even though the performance of the photodetectors is enhanced, it is not always possible to enhance the signal-to-noise ratio in the fluorescence detecting operation.

As a technique for solving the problems described above, a fluorometric analysis technique utilizing an evanescent wave has heretofore been proposed. FIG. 3 is a schematic side view showing an example of a conventional fluorescence sensor for carrying out a fluorometric analysis technique utilizing an evanescent wave. In FIG. 3 (and in FIG. 1, which will be described later), similar elements are numbered with the same reference numerals with respect to FIG. 2. Accordingly, the explanation of the similar elements will hereinbelow be omitted.

In the fluorescence sensor illustrated in FIG. 3, in lieu of the base plate 3 described above, a prism (a dielectric material block) 13 is utilized. A metal film 20 has been formed on a surface of the prism 13. Also, the exciting light 8 having been produced by the exciting light source 7 is irradiated through the prism 13 under the conditions such that the exciting light 8 may be totally reflected from the interface between the prism 13 and the metal film 20. With the constitution of the fluorescence sensor illustrated in FIG. 3, at the time at which the exciting light 8 is totally reflected from the interface described above, an evanescent wave 11 oozes out to the region in the vicinity of the interface described above, and the secondary antibody 6 is excited by the evanescent wave 11. Also, the fluorescence detecting operation is performed by the photodetector 9 located on the side of the sample 1, which side is opposite to the side of the prism 13. (In the cases of FIG. 3, the photodetector 9 is located on the upper side.)

With the fluorescence sensor illustrated in FIG. 3, the exciting light 8 is totally reflected from the aforesaid interface downwardly in FIG. 3. Therefore, in cases where the fluorescence detecting operation is performed from above, the problems do not occur in that an exciting light detection component constitutes the background with respect to a fluorescence detection signal. Also, the evanescent wave 11 is capable of reaching only a region of several hundreds of nanometers from the aforesaid interface. Therefore, the scattering from the impurities/suspended materials M contained in the sample 1 is capable of being suppressed. Accordingly, the evanescent fluorometric analysis technique described above has attracted particular attention for serving as a technique, which is capable of markedly suppressing (light) noise than with the conventional fluorometric analysis techniques, and with which the substance to be detected is capable of being fluorometrically analyzed in units of one molecule.

The fluorescence sensor illustrated in FIG. 3 is the surface plasmon enhanced fluorescence sensor, which has the sensitivity having been enhanced markedly among the fluorescence sensors utilizing the evanescent fluorometric analysis technique. With the surface plasmon enhanced fluorescence sensor, wherein the metal film 20 is formed, at the time at which the exciting light 8 is irradiated through the prism 13, the surface plasmon arises in the metal film 20, and the fluorescence is amplified by the electric field amplifying effect of the surface plasmon. A certain simulation has revealed that the fluorescence intensity in the cases described above is amplified by a factor of approximately 1,000.

The surface plasmon enhanced fluorescence sensor of the type described above is described in, for example, Japanese Patent No. 3562912. Also, as described in, for example, "1. Total Internal Reflection Fluoresence Microscopy that Enables Observation of Surfaces Only with High Image Quality", M. Tokunaga, Understanding with bio imaging, pp. 104-113, Yodosha, there has been known a fluorescence sensor, in which the fluorescence detecting operation is performed by use of the evanescent fluorometric analysis technique without the surface plasmon enhancement being utilized particularly. In such cases, the metal film 20 illustrated in FIG. 3 is omitted, such that the sample 1 may be in direct contact with the prism 13, and the fluorescent substance, such as the secondary antibody 6, is excited by the evanescent wave 11, which oozes out from the interface between the sample 1 and the prism 13.

In the cases of the surface plasmon enhanced fluorescence sensor, as described in, for example, "Surface Plasmon Field-Enhanced Fluorescence Spectroscopy Studies of the Interaction between an Antibody and Its Surface-Coupled Antigen", F. Yu et al., Analytical Chemistry, Vol. 75, pp. 2610-2617, 2003, the problems occur in that, if the fluorescent substance contained in the sample and the metal film are markedly close to each other, energy having been excited in the fluorescent substance will undergo transition to the metal film before causing the fluorescent substance to produce the fluorescence, and a phenomenon of fluorescence production failure (i.e., the so-called metal quenching) will thus arise. As described in "Optical limiting effect in a two-photon absorption dye doped solid matrix", G. S. He et al., Applied Physics Letters, Vol. 67, Issue 23, pp. 2433-2435, 1995, in order to cope with the metal quenching described above, a technique is proposed, wherein a self-organizing film (SAM) is formed on the metal film, and wherein the fluorescent substance contained in the sample and the metal film are spaced away from each other by a distance equal to at least the thickness of the SAM. In FIG. 3, the SAM is represented by the reference numeral 21.

With the fluorescence sensors as described above, wherein the difference (i.e., the so-called Stokes' shift) between the excitation wavelength for the fluorescent substance, which is currently utilized as the label, and the fluorescence wavelength is comparatively small, the problems are encountered in that the exciting light having been scattered by impurities contained in the prism is detected by the photodetector for the fluorescence detecting operation, and in that the signal-to-noise ratio of the measurement signal is thus not capable of being kept high. For example, in the cases of Cy5 described above, the fluorescence wavelength is 680 nm with respect to the excitation wavelength falling within the range of 635 nm to 645 nm, and the Stokes' shift is thus equal to at most approximately 40 nm. Therefore, ordinarily, at the time of the fluorescence detecting operation, a wavelength separation filter referred to as the sharp cut filter, such as a band pass filter, is located at a position just before the photodetector.

However, the wavelength separation capability of the aforesaid type of the filter is not sufficient for coping with the Stokes' shift as described above. Therefore, light noise often remains mixed in the measurement signal. Also, with the aforesaid type of the filter, which ordinarily has a markedly low transmittance, the problems occur in that the quantity of the fluorescence capable of being detected becomes small, and in that the signal-to-noise ratio of the measurement signal is thus caused to become low. Further, with the aforesaid type of the filter, the cost of which is high, the problems are encountered in that the cost of the fluorescence sensor is not capable of being kept low.

With the fluorescence sensor, in which the prism (the dielectric material block) is utilized and in which the fluorescent substance is excited by the evanescent wave, the problems described above are encountered. With a constitution, in which the prism is not utilized, in cases where the exciting light is detected by the photodetector due to certain reasons or in cases where the exciting light impinges upon the eyes of the sensor operator for visually detecting the fluorescence, the accuracy of the fluorescence detecting operation is affected adversely.

SUMMARY OF THE INVENTION

The primary object of the present invention is to provide a fluorescence sensor, which is capable of detecting fluorescence with a high accuracy without being affected adversely by exciting light, and which is capable of being kept small in size and low in cost.

The present invention provides a fluorescence sensor, comprising:

i) a sensor section for collecting a fluorescent substance, which acts to represent presence of a substance to be detected in a sample, and ii) an exciting light source, which produces exciting light for exciting the fluorescent substance to produce fluorescence, wherein the improvement comprises the provision of, besides the exciting light source, at least one different non-exciting light source for irradiating different non-exciting light, which varies in wavelength from the exciting light and which is substantially free from capability of exciting the fluorescent substance, to the sensor section.

The fluorescence sensor in accordance with the present invention should preferably be modified such that the fluorescence detecting operation may be performed with the evanescent fluorometric analysis technique. Specifically, the fluorescence sensor in accordance with the present invention should preferably be modified such that the fluorescence sensor is provided with:

a dielectric material block, which has been formed from a material capable of transmitting the exciting light, a sample support section for supporting the sample at a position in the vicinity of one surface of the dielectric material block, which one surface constitutes the sensor section, and an exciting light irradiating optical system for irradiating the exciting light through the dielectric material block toward an interface between the dielectric material block at a region of the one surface of the dielectric material block and a medium, which is located on the side outward from the dielectric material block at the region of the one surface of the dielectric material block, such that total reflection conditions may be satisfied.

Also, in cases where the fluorescence sensor in accordance with the present invention is constituted such that the fluorescence detecting operation may be performed with the evanescent fluorometric analysis technique as described above, the fluorescence sensor in accordance with the present invention should more preferably be modified such that a metal film is formed on the one surface of the dielectric material block, and the exciting light irradiating optical system irradiates the exciting light toward the interface between the dielectric material block and the metal film.

Further, in such cases, the fluorescence sensor in accordance with the present invention should more preferably be modified such that an inflexible film made from a hydrophobic material is formed on the metal film.

The fluorescence sensor in accordance with the present invention is provided with, besides the exciting light source, the at least one different non-exciting light source for irradiating the different non-exciting light, which varies in wavelength from the exciting light and which is substantially free from the capability of exciting the fluorescent substance, to the sensor section. Therefore, with the fluorescence sensor in accordance with the present invention, the exciting light, which has been, for example, scattered at the region of the prism described above, is mixed with the different non-exciting light coming from the different non-exciting light source and is therefore perceived visually by the persons as mixed light having a wavelength falling within a different wavelength range. In accordance with the wavelength of the different non-exciting light produced by the different non-exciting light source, the mixed light having the wavelength falling within the different wavelength range is capable of being set to be markedly different in color from the fluorescence, which ordinarily exhibits a slight difference in color from the exciting light. Accordingly, the fluorescence to be detected is capable of being discriminated clearly from the exciting light, which has been, for example, scattered at the region of the prism. The fluorescence is thus capable of being perceived accurately.

Also, with the fluorescence sensor in accordance with the present invention, a sharp cut filter, or the like, the cost of which is high, need not be used as in the conventional fluorescence sensors for discriminating the exciting light and the fluorescence, which exhibit a small difference in wavelength from each other. Therefore, the cost of the fluorescence sensor in accordance with the present invention is capable of being kept lower than the cost of the conventional fluorescence sensors of the types described above.

With the fluorescence sensor in accordance with the present invention, wherein the fluorescence detecting operation is performed with the evanescent fluorometric analysis technique by use of the dielectric material block, in cases where the exciting light is apt to be scattered in the dielectric material block, the adverse effects of the scattering of the exciting light in the dielectric material block are capable of being avoided, and therefore particularly marked effects of the capability of the accurate perception of the fluorescence are capable of being obtained.

Further, the fluorescence sensor in accordance with the present invention may be modified such that the metal film is formed on the one surface of the dielectric material block, and such that the exciting light irradiating optical system irradiates the exciting light toward the interface between the dielectric material block and the metal film. With the modification described above, since the fluorescence is amplified by the electric field amplifying effect of the surface plasmon, which is caused to occur at the metal film, the fluorescence is capable of being perceived more clearly.

Furthermore, in such cases, the fluorescence sensor in accordance with the present invention may be modified such that the inflexible film made from the hydrophobic material is formed on the metal film. With the modification described above, the problems are capable of being prevented from occurring in that the fluorescent substance contained in, for example, the sample in a liquid state is located close to the metal film such that the metal quenching may occur. Therefore, in such cases, the metal quenching described above is not caused to occur. Accordingly, the electric field amplifying effect with the surface plasmon is capable of being obtained reliably, and the fluorescence is capable of being perceived with a high sensitivity.

Also, with the fluorescence sensor in accordance with the present invention, wherein the inflexible film is made from the hydrophobic material, the problems do not occur in that the molecules, which will cause the quenching to occur, such as metal ions and dissolved oxygen present in the liquid-state sample, enter into the interior of the inflexible film. Therefore, the problems are capable of being prevented from occurring in that the molecules described above deprive the exciting light of the excitation energy. Accordingly, in such cases, a markedly high level of excitation energy is capable of being obtained, and the fluorescence is capable of being perceived with a markedly high sensitivity.

The term "inflexible film" as used herein means the film, which has the rigidity to an extent such that the film may not be deformed to a different film thickness during the ordinary use of the sensor.

DESCRIPTION OF THE PREFERRED EMBODIMENTS

The present invention will herein below be described in further detail with reference to the accompanying drawings.

Figure 1:
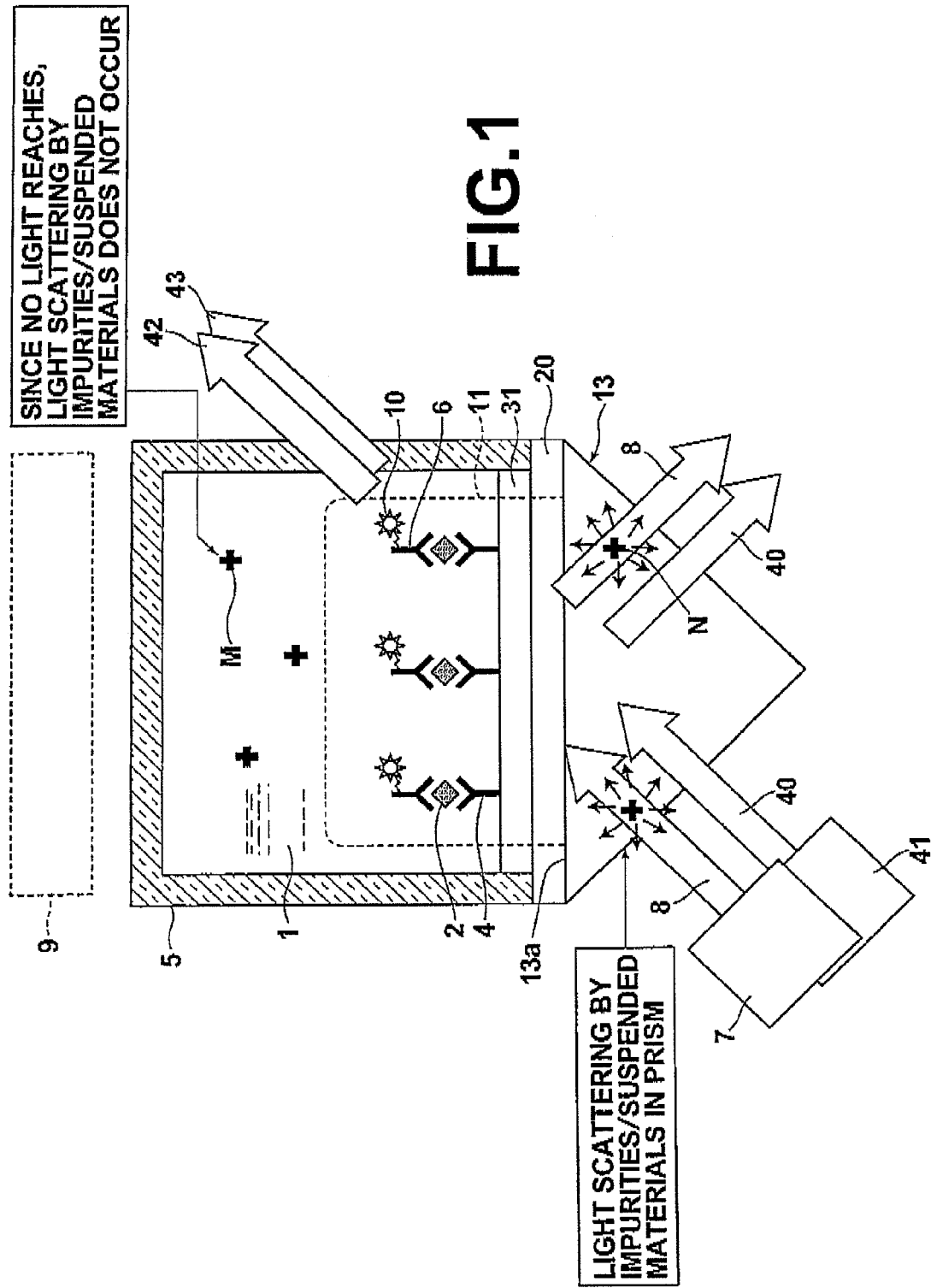
FIG. 1 is a schematic side view showing an embodiment of the fluorescence sensor in accordance with the present invention, which is constituted as a surface plasmon enhanced fluorescence sensor.
Figure 2:
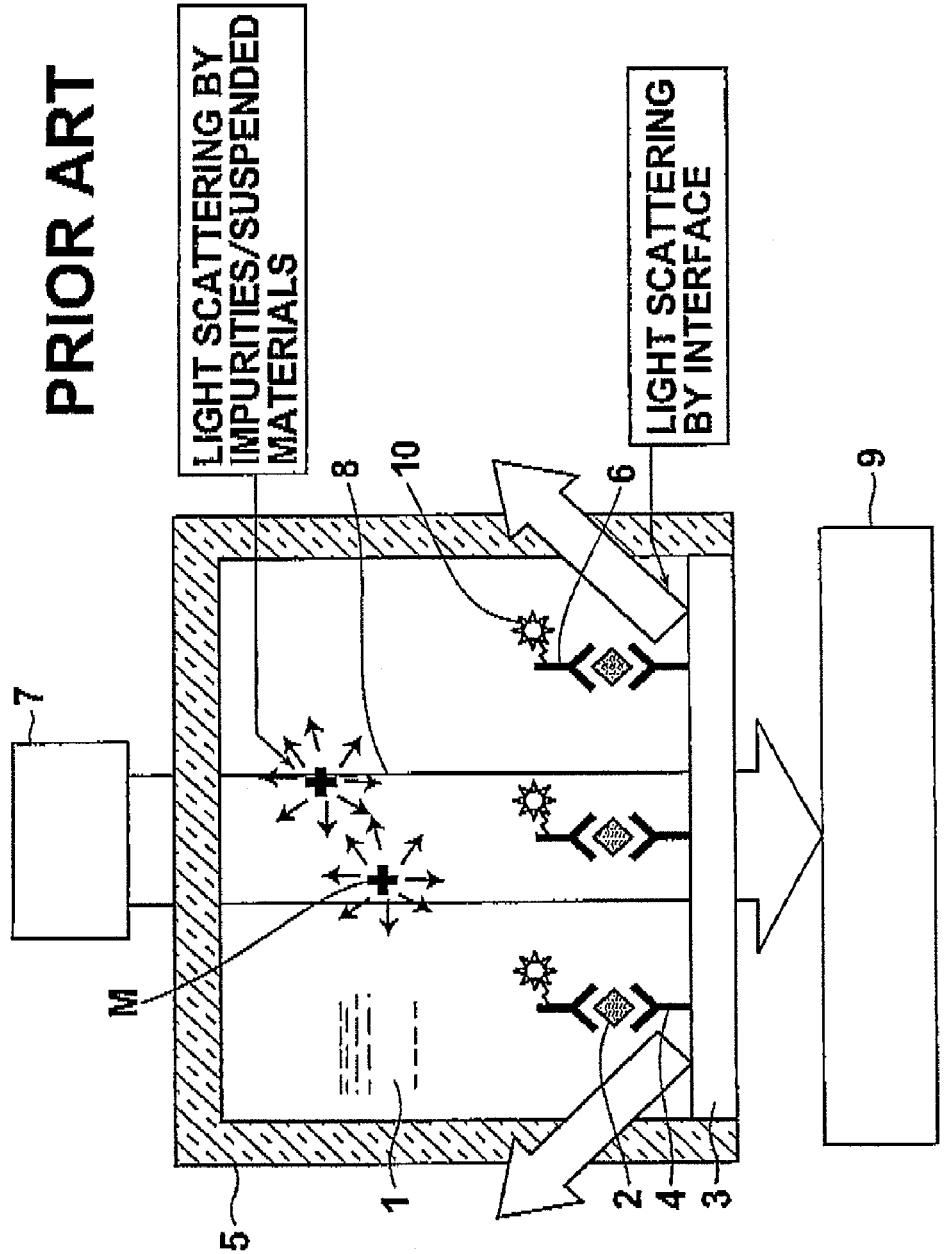
FIG. 2 is a schematic side view showing an example of a conventional fluorescence sensor for carrying out a fluorometric analysis technique utilizing a labeled specific binding substance.
Figure 3:
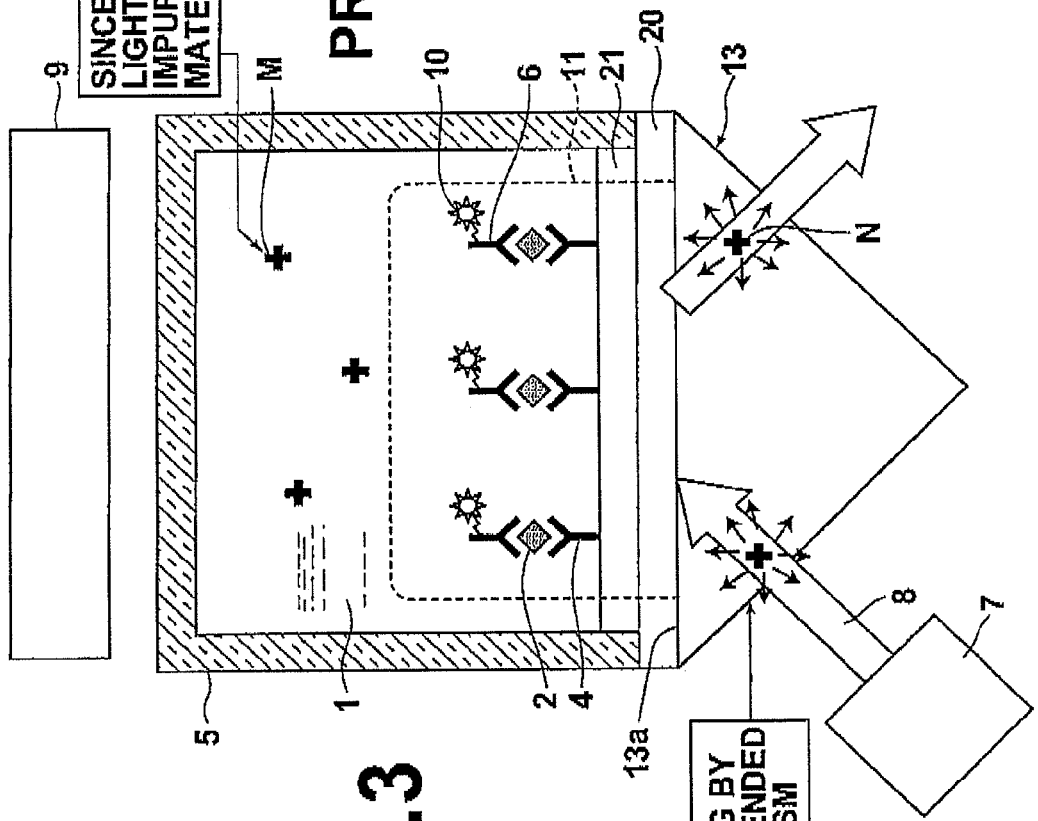
FIG. 3 is a schematic side view showing an example of a conventional fluorescence sensor for carrying out a fluorometric analysis technique utilizing an evanescent wave.

FIG. 1 is a schematic side view showing an embodiment of the fluorescence sensor in accordance with the present invention, which is constituted as a surface plasmon enhanced fluorescence sensor. (The surface plasmon enhanced fluorescence sensor, which is the embodiment of the fluorescence sensor in accordance with the present invention, will hereinbelow be referred to simply as the fluorescence sensor.) As illustrated in FIG. 1, the fluorescence sensor comprises an exciting light source 7, such as a semiconductor laser, for producing exciting light 8 having a wavelength of, for example, 650 nm. The fluorescence sensor also comprises a prism (a dielectric material block) 13, which is located such that the exciting light 8 having been produced by the exciting light source 7, may enter from one end face of the prism 13 into the interior of the prism 13. The fluorescence sensor further comprises a metal film 20, which has been formed on one surface 13a of the prism 13. The fluorescence sensor still further comprises an inflexible film 31, which has been formed on the metal film 20 and which is constituted of a polymer. The fluorescence sensor also comprises a sample support section 5 for supporting a liquid-state sample 1 such that the sample 1 may be brought into contact with the inflexible film 31 from the side opposite to the prism 13. The fluorescence sensor further comprises a non-exciting light source 41, such as a light emitting diode (LED), for irradiating non-exciting light 40 having a wavelength of, for example, 500 nm toward a region of the metal film 20, which constitutes the sensor section.

In this embodiment, the exciting light source 7 is located for irradiating the exciting light 8 through the prism 13 toward the interface between the prism 13 and the metal film 20, such that the total reflection conditions may be satisfied. Specifically, the exciting light source 7 by itself constitutes the exciting light irradiating optical system for irradiating the exciting light 8 in the manner described above with respect to the prism 13. However, the fluorescence sensor in accordance with the present invention is not limited the constitution described above. For example, alternatively, an irradiating optical system, which comprises a lens, a mirror, and the like, for irradiating the exciting light 8 in the manner described above, may be located as an independent system besides the exciting light source 7. Also, an optical system for guiding the non-exciting light 40 to the region of the metal film 20 may be located as an independent system besides the non-exciting light source 41.

By way of example, the prism 13 may be constituted of ZEONEX (trade name) 330R (refractive index: 1.50), supplied by Nippon Zeon Co., Ltd. The metal film 20 has been formed with processing, in which gold is formed on the one surface 13a of the prism 13 by use of a sputtering technique. The film thickness of the metal film 20 is set at 50 nm. Also, the inflexible film 31 has been formed with processing, in which a polystyrene type polymer having a refractive index of 1.59 is formed on the metal film 20 by use of a spin coating technique. The film thickness of the inflexible film 31 is set at 20 nm.

Besides the material described above, the prism 13 may be formed by use of a known resin, a known optical glass, or the like. From the view point of the cost, the resin is more preferable than the optical glass. In cases where the prism 13 is made from a resin, the resin may be selected appropriately from a polymethyl methacrylate (PMMA), a polycarbonate (PC), an amorphous polyolefin (APO) containing a cycloolefin, and the like.

By way of example, the object of the detection with the embodiment of the fluorescence sensor is a CRP antigen 2 (molecular weight: 110,000 Da). A primary antibody (a monoclonal antibody) 4, which is capable of undergoing the specific binding with the CRP antigen 2, has been fixed on the inflexible film 31. The primary antibody 4 has been fixed to the inflexible film 31, which is constituted of a polymer, via, for example, PEG having a terminal introduced with a carboxyl group, by use of an amine coupling technique. Also, as a secondary antibody 6, a monoclonal antibody, which has been labeled with a fluorescent substance (fluorescent dye: Cy5) 10, is employed. (The monoclonal antibody employed as the secondary antibody 6 varies in epitope (antigenic determinant) from the primary antibody 4.)

By way of example, the aforesaid amine coupling technique comprises the steps (1), (2), and (3) described below. The example described below is of the cases wherein a 30 µl (microliter) cuvette/cell is used.

(1) Activation of a —COOH Group at a Linker End (Terminal)

A solution, which has been prepared by mixing 0.1 mol of NHS and 0.4 mol of EDC together in an equal volume ratio, is added in an amount of 30 µl, and the resulting mixture is allowed to stand for 30 minutes at the room temperature.
NHS: N-Hydrooxysuccinimide
EDC: 1-Ethyl-3-(3-dimethylaminopropyl)carbodiimide (2) Fixation of the Primary Antibody 4

After washing with a PBS buffer (pH7.4) is performed five times, a primary antibody solution (500 µg/ml) is added in an amount of 30 µl, and the resulting mixture is allowed to stand for 30 to 60 minutes at the room temperature.

(3) Blocking of an Unreacted —COOH Group

After washing with the PBS buffer (pH7.4) is performed five times, 1 mol of ethanolamine (pH8.5) is added in an amount of 30 µl, and the resulting mixture is allowed to stand for 20 minutes at the room temperature. Washing with the PBS buffer (pH7.4) is then performed five times.

The exciting light source 7 is not limited to the semiconductor laser described above and may be selected from the other various kinds of the known light sources. Also, in cases where the excitation wavelength is altered, a fluorescent substance other than Cy5 is capable of being employed as a label.

How the embodiment of the fluorescence sensor operates will be described hereinbelow. Firstly, the liquid-state sample 1 is caused to flow within the sample support section 5. Thereafter, in the same manner, the secondary antibody 6, which has been labeled with the fluorescent substance 10 and which is capable of undergoing the specific binding with the CRP antigen 2, is caused to flow within the sample support section 5.

Thereafter, the exciting light 8 is irradiated from the exciting light source 7 toward the prism 13. At this time, the evanescent wave 11 oozes out from the interface between the prism 13 and the metal film 20. Therefore, in cases where the CRP antigen 2 has been bound with the primary antibody 4, the secondary antibody 6 undergoes the binding with the antigen 2, and the fluorescent substance 10 acting as the label of the secondary antibody 6 is excited by the evanescent wave 11. The fluorescent substance 10 having thus been excited by the evanescent wave 11 produces fluorescence 42 having a peak wavelength of 680 nm, and the thus produced fluorescence is perceived, for example, visually by the analysis operator. In cases where the fluorescence 42 has thus been perceived visually, it is thereby capable of being confirmed that the secondary antibody 6 has been bound with the CRP antigen 2, i.e. that the CRP antigen 2 is contained in the sample 1.

The evanescent wave 11 described above is capable of reaching only the region of approximately several hundreds of nanometers from the interface between the prism 13 and the metal film 20. Therefore, the scattering of the exciting light from the impurities/suspended materials M contained in the sample 1 is capable of being eliminated approximately perfectly.

At the time at which the fluorescence detecting operation is performed in the manner described above, it may often occur that the exciting light 8 is scattered by impurities N contained in the prism 13. Also, it may often occur that the exciting light 8 having thus been scattered by the impurities N contained in the prism 13 does not satisfy the total reflection conditions described above, and that a part of the thus scattered exciting light 8 passes through the metal film 20 and is radiated out upwardly from the metal film 20. The wavelength of the exciting light 8 is 650 nm and thus falls within the red region as in the cases of the fluorescence 42 having the wavelength of 680 nm. Therefore, it is not always possible to make the visual discrimination between the exciting light 8 and the fluorescence 42. Accordingly, it is not always possible to make a judgment as to whether the fluorescence 42 has or has not been produced actually, i.e. whether the CRP antigen 2 is or is not present in the sample 1.

In this embodiment of the fluorescence sensor in accordance with the present invention, in order for the aforesaid problems to be eliminated, the non-exciting light source 41 is provided. The non-exciting light source 41 is actuated together with the exciting light source 7 at the time of the fluorescence detecting operation. The non-exciting light 40 having the wavelength of 500 nm, which light is radiated out from the non-exciting light source 41 toward the region of the metal film 20, is scattered by the impurities N contained in the prism 13 as in the cases of the exciting light 8, and a part of the thus scattered non-exciting light 40 passes through the metal film 20 and is radiated out upwardly from the metal film 20. Therefore, mixed light 43, which is a mixture of the non-exciting light 40 having the wavelength of 500 nm and the exciting light 8 having the wavelength of 650 nm, is seen by the analysis operator. The mixed light 43 is visually perceived by persons as approximately yellow light and is therefore capable of being clearly discriminated from the light having the wavelength falling within the red region. Accordingly, in cases where yellow light is perceived at the region of the metal film 20, the analysis operator is capable of judging that the fluorescence 42 has not been produced. Also, in cases where approximately red light (i.e., mixed light resulting from the mixing of the non-exciting light 40 having the wavelength of 500 nm, the exciting light 8 having the wavelength of 650 nm, and the fluorescence 42 having the wavelength of 680 nm with one another) is perceived at the region of the metal film 20, the analysis operator is capable of judging that the fluorescence 42 has been produced, i.e. that the CRP antigen 2 is present in the sample 1.

Also, with this embodiment of the fluorescence sensor, wherein the inflexible film 31 having a film thickness of 20 nm is formed on the metal film 20, the problems are capable of being prevented from occurring in that the fluorescent substance 10 contained in the sample 1 becomes close to the metal film 20 to an extent such that the metal quenching may occur. Therefore, with this embodiment of the fluorescence sensor, the metal quenching described above is not caused to occur. Accordingly, the electric field amplifying effect with the surface plasmon is capable of being obtained reliably, and the fluorescence is capable of being detected with a high sensitivity.

Further, with this embodiment of the fluorescence sensor, wherein the inflexible film 31 is made from the polystyrene type polymer, which is the hydrophobic material, the problems do not occur in that the molecules, which will cause the quenching to occur, such as metal ions and dissolved oxygen present in the liquid-state sample 1, enter into the interior of the inflexible film 31. Therefore, the problems are capable of being prevented from occurring in that the molecules described above deprive the exciting light 8 of the excitation energy. Accordingly, with this embodiment of the fluorescence sensor, a markedly high level of excitation energy is capable of being obtained, and the fluorescence is capable of being detected with a markedly high sensitivity.

In this embodiment of the fluorescence sensor, the evanescent wave 11 does not reach the secondary antibody 6, which has not been bound with the CRP antigen 2 and is spaced away from the surface of the inflexible film 31. Therefore, the secondary antibody 6, which has not been bound with the CRP antigen 2 and is spaced away from the surface of the inflexible film 31, does not produce the fluorescence. Accordingly, in cases where the secondary antibody 6 as described above is being suspended in the sample 1, no problems occur with respect to the measurement, and a washing operation, i.e. a B/F separating operation (a bound/free separating operation) need not be performed for each stage of the measurement.

Furthermore, the fluorescence sensor in accordance with the present invention may be provided with a photodetector 9 indicated by the broken line in FIG. 1. In cases where the fluorescence 42 has been perceived by the analysis operator, the intensity of the fluorescence 42 may be detected by the photodetector 9. In cases where the quantity of the CRP antigen 2 present in the sample 1 is large, the fluorescence intensity becomes high. Therefore, a quantitative analysis of the CRP antigen 2 is capable of being made in accordance with the fluorescence intensity having thus been detected.

Also, the wavelength and the number of beams of the non-exciting light 40 irradiated to the region of the metal film 20 together with the exciting light 8 are not limited to those employed in the embodiment described above. Specifically, for example, the exciting light 8 having the wavelength falling within the red region and the non-exciting light 40 having a wavelength falling within a cyan region are irradiated together to the sensor section, white light is obtained as the mixed light 43, which results from the mixing of the exciting light 8 and the non-exciting light 40. The white light thus obtained as the mixed light 43 is capable of being discriminated clearly from the fluorescence 42 having the wavelength falling within the red region. Further, in lieu of the non-exciting light 40 having the wavelength falling within the cyan region, a light beam having a wavelength falling within a blue region and a light beam having a wavelength falling within a green region may be employed. In such cases, white light is obtained as the mixed light 43.

Furthermore, the fluorescence sensor in accordance with the present invention may be modified such that the metal film 20 is not provided, and such that the surface plasmon enhancement is not performed. Also, the fluorescence sensor in accordance with the present invention may be modified such that, instead of the fluorescent substance 10 being excited by the evanescent wave 11, the fluorescent substance 10 is excited by the exciting light, which is the ordinary propagated light. With each of the two modifications described above, in cases where the different non-exciting light is irradiated to the sensor section together with the exciting light, the effects described above are capable of being obtained.

What is claimed is:

1. A fluorescence sensor, comprising:
   a sensor section for collecting a fluorescent substance, which acts to represent presence of a substance to be detected in a sample;
   an exciting light source, which produces exciting light for exciting the fluorescent substance to produce fluorescence; and
   at least one different non-exciting light source for irradiating different non-exciting light, which varies in wavelength from the exciting light and which is substantially free from capability of exciting the fluorescent substance, to the sensor section,
   wherein the fluorescence sensor is provided with:

a dielectric material block, which has been formed from a material capable of transmitting the exciting light, a sample support section for supporting the sample at a position in the vicinity of one surface of the dielectric material block, which one surface constitutes the sensor section, and an exciting light irradiating optical system for irradiating the exciting light through the dielectric material block toward an interface between the dielectric material block at a region of the one surface of the dielectric material block and a medium, which is located on the side outward from the dielectric material block at the region of the one surface of the dielectric material block, such that total reflection conditions may be satisfied.

2. A fluorescence sensor as defined in claim 1 wherein the exciting light source produces the exciting light having a wavelength falling within a red region, and the different non-exciting light source produces the different non-exciting light having a wavelength falling within a green region.

3. A fluorescence sensor as defined in claim 1 wherein the exciting light source produces the exciting light having a wavelength falling within a red region, and the different non-exciting light source produces the different non-exciting light having a wavelength falling within a cyan region.

4. A fluorescence sensor as defined in claim 1 wherein the exciting light source produces the exciting light having a wavelength falling within a red region, and the fluorescence sensor is provided with two different non-exciting light sources, one of the two different non-exciting light sources producing the different non-exciting light having a wavelength falling within a blue region, the other different non-exciting light source producing the different non-exciting light having a wavelength falling within a green region.

5. A fluorescence sensor as defined in claim 1 wherein a metal film is formed on the one surface of the dielectric material block, and the exciting light irradiating optical system irradiates the exciting light toward the interface between the dielectric material block and the metal film.

6. A fluorescence sensor as defined in claim 5 wherein an inflexible film made from a hydrophobic material is formed on the metal film.

7. A fluorescence sensor as defined in claim 6 wherein the inflexible film is constituted of a polymer.

8. A fluorescence sensor as defined in claim 6 wherein a substance for attracting the fluorescent substance has been fixed onto the inflexible film.

9. A fluorescence sensor as defined in claim 8 wherein the substance, which has been fixed onto the inflexible film, is an antibody that is capable of undergoing binding with an antigen capable of undergoing the binding with the fluorescent substance.

* * * * *